(12) United States Patent
Hayakawa et al.

(10) Patent No.: US 9,462,870 B2
(45) Date of Patent: Oct. 11, 2016

(54) AQUEOUS MANICURE PREPARATION AND MANICURE PREPARATION-FILLED APPLICATOR

(75) Inventors: Takayuki Hayakawa, Fujioka (JP); Kei Omoto, Fujioka (JP)

(73) Assignee: MITSUBISHI PENCIL COMPANY, LIMITED, Tokyo (JP)

( * ) Notice: Subject to any disclaimer, the term of this patent is extended or adjusted under 35 U.S.C. 154(b) by 634 days.

(21) Appl. No.: 13/128,295

(22) PCT Filed: Nov. 11, 2009

(86) PCT No.: PCT/JP2009/069156
§ 371 (c)(1),
(2), (4) Date: May 9, 2011

(87) PCT Pub. No.: WO2010/055838
PCT Pub. Date: May 20, 2010

(65) Prior Publication Data
US 2011/0222956 A1    Sep. 15, 2011

(30) Foreign Application Priority Data
Nov. 11, 2008    (JP) .................................. 2008-288769

(51) Int. Cl.
| | | |
|---|---|---|
| A45D 29/11 | (2006.01) | |
| A61Q 3/02 | (2006.01) | |
| A61K 8/73 | (2006.01) | |
| A61K 8/891 | (2006.01) | |
| A45D 34/04 | (2006.01) | |

(52) U.S. Cl.
CPC .............. *A45D 34/04* (2013.01); *A61K 8/731* (2013.01); *A61Q 3/02* (2013.01); *A45D 34/048* (2013.01); *A61K 2800/87* (2013.01)

(58) Field of Classification Search
None
See application file for complete search history.

(56) References Cited

U.S. PATENT DOCUMENTS

| | | | | |
|---|---|---|---|---|
| 6,264,934 | B1 * | 7/2001 | Kantner et al. .............. | 424/78.03 |
| 2003/0123922 | A1 * | 7/2003 | Kabayashi ............... | B43K 1/08 401/206 |
| 2006/0134045 | A1 * | 6/2006 | Cao et al. .................. | 424/70.13 |
| 2009/0116895 | A1 | 5/2009 | Uehara et al. | |

FOREIGN PATENT DOCUMENTS

| | | | |
|---|---|---|---|
| JP | 6-227945 | A | 8/1994 |
| JP | 9-071511 | A | 3/1997 |
| JP | 9-71511 | A | 3/1997 |
| JP | 9-071521 | A | 3/1997 |
| JP | 9-110642 | A | 4/1997 |
| JP | 11179269 | * | 7/1999 |
| JP | 11-269041 | A | 10/1999 |
| JP | 2000-159628 | A | 6/2000 |
| JP | 2000-247833 | A | 9/2000 |
| JP | 2002-114641 | A | 4/2002 |
| JP | 2004-059035 | A | 2/2004 |
| JP | 2004-244321 | A | 9/2004 |
| JP | 2005-289969 | A | 10/2005 |
| JP | 2006-043888 | A | 2/2006 |
| JP | 2006-160683 | A | 6/2006 |
| WO | WO 2007/043555 | A1 | 4/2007 |
| WO | 2008087508 | A2 | 7/2008 |

OTHER PUBLICATIONS

Notification of Transmittal of Translation of the International Preliminary Report on Patentability (Form PCT/IB/338) from the International Bureau of WIPO issued in corresponding International Patent Application No. PCT/JP2009/069156 dated Jun. 30, 2011.
English version of International Preliminary Report on Patentability (Form PCT/IB/373) from the International Bureau of WIPO issued in corresponding International Patent Application No. PCT/JP2009/069156 dated Jun. 21, 2011.
English translation of Written Opinion of the International Searching Authority (Form PCT/ISA/237) from the International Bureau of WIPO issued in corresponding International Patent Application No. PCT/JP2009/069156.
International Search Report (PCT/ISA/210) issued on Feb. 9, 2010, by Japanese Patent Office as the International Searching Authority for International Application No. PCT/JP2009/069156.
Communication pursuant to Article 153(7) EPC issued on Sep. 10, 2014 by the European Patent Office in corresponding European Patent Application No. 09826085.4-1464 (PCT/JP2009069156) (5 pages).

* cited by examiner

*Primary Examiner* — Robert A Wax
*Assistant Examiner* — Randeep Singh
(74) *Attorney, Agent, or Firm* — Buchanan Ingersoll & Rooney PC (57) ABSTRACT

An aqueous manicure preparation which is an aqueous cosmetic preparation for a nail art wherein in an applicator which is equipped with at least a liquid storing part and an applying member and in which a liquid is transported from the liquid storing part to the applying member by virtue of capillary force, the aqueous manicure preparation stored in the liquid storing part contains at least water, a water-soluble resin, a tabular pigment, an emulsion resin, a moisturizing agent and a fungicide and further contains crystalline cellulose and has a viscosity satisfying the following condition (A) in measuring the viscosity at a temperature of 25° C. by means of a cone plate type viscometer:

| (A) shear rate ($s^{-1}$) | viscosity (mPa · s) |
|---|---|
| 3.83 | 30 to 150 |
| 19.15 | 10 to 50 |
| 38.30 | 10 to 40 |
| 76.60 | 10 to 40 |
| 383.00 | 5 to 20. |

10 Claims, 3 Drawing Sheets

AQUEOUS MANICURE PREPARATION AND MANICURE PREPARATION-FILLED APPLICATOR

TECHNICAL FIELD

The present invention relates to an aqueous manicure preparation and a manicure preparation-filled applicator which are used for drawing fine lines and patterns on a nail.

BACKGROUND ART

A manicure preparation has so far been classified roughly into an organic solvent base and an aqueous base according to purposes and characteristics thereof. A manicure preparation of an organic solvent base is excellent in a coating property and a quick drying property but has a problem that a nail and a skin are roughened. In contrast with this, an aqueous manicure preparation exerts less influence on a body, and a lot of aqueous manicure preparations have been developed in recent years.

Known as conventional aqueous manicure preparations are, for example, 1) an aqueous manicure preparation containing a kneaded composition prepared by kneading a powder into an anionic acryl resin (refer to, for example, patent document 1), 2) an aqueous manicure preparation characterized by blending an acrylic polymer emulsion with a powder subjected to hydrophilic treatment with a silylation agent having a polyoxyethylene chain (refer to, for example, patent document 2), 3) an aqueous manicure preparation containing a brilliant pearly pigment prepared by coating at least one kind of a colorant on glass flakes in a single layer and an aqueous polymer emulsion (refer to, for example, patent document 3) and 4) an aqueous manicure preparation containing a pearl pigment prepared by coating two or more kinds of light transmissive materials having different refractive indices on a flaky base material in plural layers and an aqueous polymer emulsion (refer to, for example, patent document 4).

However, the respective aqueous manicure preparations described in the above patent documents 1 to 4 have the problem that the cosmetics have a high viscosity to make it impossible to draw fine lines and patterns on a nail. Further, the pearly pigments and the pearl pigments in which brilliance is obtained by reflecting light have a larger particle diameter than those of conventional organic pigments and inorganic pigments and are constituted mainly of tabular pigments, and therefore if aqueous manicure preparations containing the above tabular pigments are low in a viscosity, involved therein is the problem that the tabular pigments settle down and that the particles are not evenly dispersed well even by stirring again and form a hard cake.

Further, if conventional aqueous manicure preparations are low in a viscosity, involved therein is the problem that when fine lines and patterns are drawn on a nail, cissing is marked in a case of narrow drawn lines to make it impossible to draw fine lines and patterns.

Further, a brush obtained by bunching fibers which has so far been used for manicure preparations as an applicator for drawing fine lines and patterns on a nail is suited for applying them on a whole part of a nail, but when drawing lines and the like, defects such as spilling of the cosmetics have been brought about. Further, a so-called pen feed and the like which are prepared by fixing fiber bundles with a binder involve the problem that a tabular pigment brings about clogging in the pen feed to make it impossible to draw fine lines.

On the other hand, the present applicants have filed a liquid cosmetic suited for eye makeup, wherein it contains 5 to 25% by weight of a pearl pigment comprising basically an inorganic substance which contains mica, titanium dioxide coated mica or a surface-treated substance thereof and 0.2 to 2.0% by weight of an anionic polymer compound such as a xanthan gum and the like; a non-Newtonian viscosity index (n) falls in a range of $0.16 \leq n \leq 0.28$; and a viscosity falls in a specific range at a prescribed shear rate (refer to, for example, patent document 5).

The above liquid cosmetic discloses a technique close to the present invention, but it is a cosmetic used for a skin such as eye makeup and the like and therefore is entirely different in a use thereof from a cosmetic coated on a nail, and it has a high viscosity and falls in an apparently different viscosity range. In addition thereto, involved therein is the problem that in a case of an aqueous manicure preparation having a low viscosity, stabilization and redispersibility of a tabular pigment can not be exerted well even by using a xanthan gum and the like.

On the other hand, known are a cosmetic composition characterized by blending particles of at least one material selected from organic polymers, oil & fats, waxes, mineral oils, inorganic substances and plants which comprise granules having a shape factor falling in a range of 0.98 to 0.50 and a particle diameter falling in a range of 50 to 2000 µm in a circularity coefficient of 0.98 to 0.40 and a cosmetic composition used effectively for detergents, massaging agents, cleansing agents and the like in which granules prepared by granulating water-insoluble primary particles using a binder such as crystalline cellulose and the like are granules having a shape factor falling in a range of 0.98 to 0.50 and a particle diameter falling in a range of 50 to 2000 µm in a circularity coefficient of 0.98 to 0.40 (refer to, for example, patent document 6).

In the above granule-blended cosmetic composition, it is disclosed in Production Example 3 (paragraph 0082) to use crystalline cellulose, but the crystalline cellulose is shown as an example of a binder, and it is different in a technical concept (purposes, a constitution and an operation and effect) from the present invention.

PRIOR ART REFERENCES

Patent Documents

Patent document 1: Japanese Patent Application Laid-Open Hei 9 No. 71521
Patent document 2: Japanese Patent Application Laid-Open Hei 9 No. 110642
Patent document 3: Japanese Patent Application Laid-Open No. 2004-244321
Patent document 4: Japanese Patent Application Laid-Open No. 2006-160683
Patent document 5: Japanese Patent Application Laid-Open No. 2000-247833
Patent document 6: Japanese Patent Application Laid-Open No. 2000-159628

OUTLINE OF THE INVENTION

Problems to be Solved by the Invention

In light of the problems on the conventional techniques described above, the present invention intends to solve them, and an object thereof is to provide an aqueous manicure preparation which is excellent in an aging precipitation stability as an aqueous manicure preparation suited in an applicator for drawing fine lines and patterns on a nail and less liable to form a hard cake even when a tabular pigment settles down to make it possible to readily redisperse it by stirring and which is excellent in usability to make it possible to readily draw fine lines and patterns on a nail and excellent in a finishing property and an aqueous manicure preparation-filled applicator.

Means for Solving Problems

In light of the problems on the conventional techniques described above, the present inventors intended to solve them, and have found that in an applicator which is equipped with at least a liquid storing part and an applying member and in which a liquid is transported from the liquid storing part to the applying member by virtue of capillary force, an aqueous manicure preparation stored in the liquid storing part described above contains at least water, a water-soluble resin, a tabular pigment, an emulsion resin, a moisturizing agent and a fungicide and is provided with a surface tension falling in a specific value, and it further contains crystalline cellulose and is provided with a viscosity falling in a specific range in a prescribed shear rate at a temperature of 25° C., whereby an aqueous manicure preparation and an aqueous manicure preparation-filled applicator which meet the object described above are obtained. Thus, the present invention has come to be completed.

That is, the present invention comprises the following items (1) to (9).

(1) An aqueous manicure preparation characterized in that in an applicator which is equipped with at least a liquid storing part and an applying member and in which a liquid is transported from the liquid storing part to the applying member by virtue of capillary force, the aqueous manicure preparation stored in the liquid storing part contains at least water, a water-soluble resin, a tabular pigment, an emulsion resin, a moisturizing agent and a fungicide and is provided with a surface tension of 33 dyn/cm or less and that it further contains crystalline cellulose and is provided with a viscosity satisfying the following condition (A) in measuring the viscosity at a temperature of 25° C. by means of a cone-plate type viscometer:

| (A) shear rate ($s^{-1}$) | viscosity (mPa · s) |
|---|---|
| 3.83 | 30 to 150 |
| 19.15 | 10 to 50 |
| 38.30 | 10 to 40 |
| 76.60 | 10 to 40 |
| 383.00 | 5 to 20 |

(2) The aqueous manicure preparation as described in the above item (1), wherein a value of n in the following equation (I) falls in a range of 0.5 to 0.7:

$$S=\mu D^n \quad (I)$$

(in the equation (I), S is a shear stress (Pa); $\mu$ is a viscosity coefficient (viscosity: Pa·S); D is a shear rate ($s^{-1}$); and n is a non-Newtonian viscosity index).

(3) The aqueous manicure preparation as described in the above item (1) or (2), wherein the water-soluble resin accounts for 0.008 to 2.0% by mass; the tabular pigment accounts for 1.0 to 20.0% by mass; the emulsion resin accounts for 4.5 to 13.5% by mass in terms of a solid content; and a total of the fungicides accounts for 0.01 to 10.0% by mass.

(4) The aqueous manicure preparation as described in any of the above items (1) to (3), wherein the crystalline cellulose accounts for 0.5 to 10.0% by mass.

(5) The aqueous manicure preparation as described in any of the above items (1) to (4), wherein the moisturizing agent accounts for 8 to 15% by mass.

(6) The aqueous manicure preparation as described in any of the above items (1) to (5), wherein the aqueous manicure preparation further contains at least polydimethylsiloxane.

(7) An aqueous manicure preparation-filled applicator which is equipped with a liquid storing part stored with the aqueous manicure preparation as described in any of the above items (1) to (6) and an applying member and in which the aqueous manicure preparation is transported from the liquid storing part to the applying member by virtue of capillary force, wherein the applying member is provided with capillary force.

(8) The aqueous manicure preparation-filled applicator as described in the above item (7), wherein the applying member provided with capillary force is equipped with a tubular inner cylinder, and a tip thereof is conical and is provided with a slit in radial pattern.

(9) The aqueous manicure preparation-filled applicator as described in the above item (7) or (8), wherein a porous member having continuous pores is provided in a passage of the aqueous manicure preparation extending from the liquid storing part to the applying member.

Effects of the Invention

According to the present invention, provided are an aqueous manicure preparation which is excellent in an aging precipitation stability and less liable to form a hard cake even when a tabular pigment settles down to make it possible to readily redisperse it by stirring and which is excellent in usability to make it possible to readily draw fine lines and patterns on a nail and excellent in a finishing property and an aqueous manicure preparation-filled applicator.

MODE FOR CARRYING OUT THE INVENTION

The embodiments of the present invention shall be explained below in detail.

The aqueous manicure preparation of the present invention is characterized in that in an applicator which is equipped with at least a liquid storing part and an applying member and in which a liquid is transported from the liquid storing part to the applying member by virtue of capillary force, the aqueous manicure preparation stored in the liquid storing part described above contains at least water, a water-soluble resin, a tabular pigment, an emulsion resin, a moisturizing agent and a fungicide and is provided with a surface tension of 33 dyn/cm or less and that it further contains crystalline cellulose and is provided with a viscosity satisfying the following condition (A) in measuring the viscosity at a temperature of 25° C. by means of a cone-plate type viscometer:

| (A) shear rate (s$^{-1}$) | viscosity (mPa · s) |
|---|---|
| 3.83 | 30 to 150 |
| 19.15 | 10 to 50 |
| 38.30 | 10 to 40 |
| 76.60 | 10 to 40 |
| 383.00 | 5 to 20 |

Further, in the aqueous manicure preparation of the present invention, a value of n in the following equation (I) falls preferably in a range of 0.5 to 0.7:

$$S = \mu D^n \quad (I)$$

(in the equation (I), S is a shear stress (Pa); μ is a viscosity coefficient (viscosity: Pa·S); D is a shear rate (s$^{-1}$); and n is a non-Newtonian viscosity index).

The tabular pigment used in the present invention includes, for example, mica, titanium dioxide coated mica, carmine-titanium dioxide coated mica, prussian blue-titanium dioxide coated mica, black iron oxide-titanium dioxide coated mica, black iron oxide-carmine-titanium dioxide coated mica, black iron oxide-prussian blue-titanium dioxide coated mica, prussian blue-titanium dioxide coated mica, iron oxide red-coated mica, iron oxide red-titanium dioxide coated mica, iron oxide red-carmine-titanium dioxide coated mica, iron oxide red-black iron oxide-titanium dioxide coated mica, iron oxide red-prussian blue-titanium dioxide coated mica, iron oxide red-black iron oxide-prussian blue-titanium dioxide coated mica and the like, and it further includes brilliant pigments prepared by coating metal or metal oxide on a glass flake or a massive flake used as a base material. The above tabular pigments each may be used alone or in combination of two or more kinds thereof.

A content of the tabular pigments is preferably 1 to 20% by mass, more preferably 5 to 15% by mass based on a total amount of the aqueous manicure preparation in order to obtain good drawn lines, a good coating performance and good use characteristics.

If a content of the tabular pigments is less than 1% by mass, the brilliance and the coated color are faint and not fine. On the other hand, if it is in excess of 20% by mass, the viscosity is high to make it impossible to draw fine lines, and the liquid is decreased in flowing from the applying member or clogging is liable to be brought about in the applying member.

The water-soluble resin used in the present invention functions as a coating film-forming agent and a dispersion stabilizer, and it includes, to be specific, copolymers comprising monomers selected from at least one of acrylic acid, methacrylic acid, alkyl esters thereof or derivatives thereof. To be more specific, preferred are copolymers which have an acid group in a composition and which can be dissolved in water by neutralization.

Copolymers of tert-butyl acrylate, ethyl acrylate and methacrylic acid are particularly preferred. Meanwhile, 2-amino-2-methyl-1-propanol, 2-amino-2-methyl-1,3-propanediol, triethanolamine, L-arginine, aqueous ammonia, sodium hydroxide and the like can be used for the neutralization, and 2-amino-2-methyl-1-propanol is particularly preferred.

A content of the above water-soluble resins is preferably 0.008 to 2.0% by mass, more preferably 0.1 to 1.5% by mass based on a total amount of the aqueous manicure preparation.

If a content of the water-soluble resins is less than 0.008% by mass, the precipitation stability and the redispersibility are deteriorated, and the finishing is not fine. On the other hand, if it is in excess of 20% by mass, the viscosity is high to make it impossible to draw fine lines.

The emulsion resin used in the present invention functions as a coating film-forming agent and a dispersion stabilizer, and it includes, to be specific, emulsions of copolymers comprising two or more kinds of monomers selected from alkyl acrylates, alkyl methacrylates, acrylic acid and methacrylic acid (alkyl acrylate copolymer emulsions) and emulsions of copolymers comprising at least one component selected from alkyl acrylates, alkyl methacrylates, acrylic acid and methacrylic acid and styrene (alkyl acrylate.styrene copolymer emulsions).

A content of the emulsion resins is preferably 4.5 to 13.5% by mass, more preferably 6.5 to 11.5% by mass in terms of a solid content based on a total amount of the aqueous manicure preparation.

If a content of the emulsion resins is less than 4.5% by mass in terms of a solid content, redispersibility of the pigment is deteriorated, and a fixing property of the drawn lines grows worse. On the other hand, if it is in excess of 13.5% by mass, finishing of the drawn lines is deteriorated, and the applying member is likely to be dried to make coating impossible.

The fungicide used in the present invention includes parabens, sodium dehydroacetate, phenoxyethanol and the like. Antiseptic agents are included in the fungicide used in the present invention, and methyl paraoxybenzoate, ethyl paraoxybenzoate, propyl paraoxybenzoate, butyl paraoxybenzoate, isopropyl paraoxybenzoate and the like can be used as parabens which are antiseptic agents.

A total content of the fungicides is preferably 0.01 to 10.0% by mass, more preferably 0.1 to 5.0% by mass based on a total amount of the aqueous manicure preparation.

If a content of the fungicides is less than 0.01% by mass in terms of a solid content, it is difficult to inhibit propagation of microorganisms. On the other hand, if it is in excess of 10.0% by mass, involved therein are the problems that inferior dissolution of the antiseptic agent is brought about and that blending limitation thereof is exceeded.

The crystalline cellulose used in the present invention functions as a pigment dispersant and a thickener, and it is, to be specific, a cellulose crystallite aggregate which is obtained by subjecting cellulose to hydrolysis with acid or oxidation decomposition with alkali and which has a substantially fixed polymerization degree. It has the characteristic that cellulose crystal becomes a dispersed particle in water unlike a conventional aqueous solution of thickening polysaccharides.

The crystalline cellulose which can be used includes, for example, substances comprising colloidal grade which are obtained by subjecting surfaces of fine cellulose crystals of primary particles to a coating treatment with a water-soluble polymer and the like, and the specific examples thereof include Ceolus RC-591, RC-N81, RC-591NF and CL-611 and Ceolus Cream (each manufactured by Asahi Kasei Chemicals Corporation).

A content of the crystalline celluloses is preferably 0.5 to 10% by mass, more preferably 1.0 to 5.0% by mass based on a total amount of the aqueous manicure preparation.

If a content of the crystalline celluloses is less than 0.5% by mass, the tabular pigment can not be inhibited from settling down and is separated soon. On the other hand, if it exceeds 10% by mass, the liquid is too higher in a viscosity and can not be discharged by a discharge mechanism in the vessel of the present invention, and therefore it is not preferred.

The moisturizing agent is contained in the aqueous manicure preparation of the present invention for the purpose of improving the finishing.

The moisturizing agent which can be used includes, for example, glycols which are soluble in water, such as 1,3-butylene glycol, 1,4-butylene glycol, pentylene glycol, ethylene glycol, diethylene glycol, polyethylene glycol, propylene glycol, dipropylene glycol, glycerin and the like.

A content of the moisturizing agents is 1 to 20% by mass, preferably 8 to 15% by mass based on a total amount of the aqueous manicure preparation.

If a content of the above moisturizing agents (glycols which are soluble in water) is less than 1% by mass, fitting to the base material is inferior though a reason therefor is uncertain, and peeling is brought about so that the finishing is not fine. On the other hand, if it exceeds 20% by mass, time for drying is extended, and inconvenience is brought about in handling.

In addition to the components described above, polydimethylsiloxane is preferably contained as a defoaming agent in the aqueous manicure preparation of the present invention.

Polydimethylsiloxane is a silicone oil comprising a mixture of linear siloxane polymers in which ends thereof are blocked by a trimethylsiloxane unit to be methylated, and KS-66 (manufactured by Shin-Etsu Silicones Co., Ltd.) and the like can be used as commercial products.

A content of the above polydimethylsiloxanes is used in a range of preferably 0.0001 to 0.01% by mass, more preferably 0.0005 to 0.001% by mass based on a total amount of the aqueous manicure preparation.

If a content of the polydimethylsiloxanes is less than 0.0001% by mass, an effect of adding polydimethylsiloxane is reduced. On the other hand, if it exceeds 0.01% by mass, the finishing is deteriorated.

The respective components described above are contained in the aqueous manicure preparation of the present invention, and the balance thereof is controlled by water (refined water, ion-exchanged water, distilled water and the like). A surface tension thereof (25° C.) is controlled to 33 dyn/cm or less, preferably 25 to 33 dyn/cm so that cissing is not marked when drawing narrow lines and the like on a nail.

If the surface tension exceeds 33 dyn/cm, cissing is caused on a nail in a certain case, and therefore it is not preferred.

In the present invention, dioctyl sodium sulfosuccinate (NIKKOL OTP-75 of a commercial product) and the like can be used as a component which controls the surface tension of the aqueous manicure preparation to the characteristic value described above or lower.

In the aqueous manicure preparation of the present invention, a viscosity thereof has to satisfy the following condition (A) in measuring the viscosity at a temperature of 25° C. by means of a cone plate type viscometer:

| (A) shear rate ($s^{-1}$) | viscosity (mPa · s) |
|---|---|
| 3.83 | 30 to 150 |
| 19.15 | 10 to 50 |
| 38.30 | 10 to 40 |

-continued

| (A) shear rate ($s^{-1}$) | viscosity (mPa · s) |
|---|---|
| 76.60 | 10 to 40 |
| 383.00 | 5 to 20 |

The aqueous manicure preparation deviating from the viscosity range in the prescribed shear rates described above is inferior in usuability of the product and deteriorated in finishing, and therefore it is not preferred.

In order to satisfy the condition (A) described above, the crystalline cellulose, the water-soluble resin, the tabular pigment and the like which are added to the aqueous manicure preparation are suitably combined and controlled in the ranges of the respective contents described above, whereby the aqueous manicure preparation can be prepared.

In the aqueous manicure preparation of the present invention, a value of n in the following equation (I) falls preferably in a range of 0.5 to 0.7:

$$S = \mu D^n \quad (I)$$

(in the equation (I), S is a shear stress (Pa); μ is a viscosity coefficient (viscosity: Pa·S); D is a shear rate ($s^{-1}$); and n is a non-Newtonian viscosity index).

If the value of n is less than 0.5, it is likely that the aqueous manicure preparation does not flow out from an inside of the applicator, and therefore it is not preferred. Also, if the above value of n exceeds 0.7, dripping of the manicure preparation from the applying member of the applicator or flowing of the manicure preparation on a nail before drying after applying the manicure preparation is likely to be brought about, and therefore it is not preferred as well.

In addition to the respective components described above, ethylenediaminetetraacetic acid, ethylenediaminehyroxyethyltriacetic acid and monosodium salts, disodium salts and trisodium salts thereof may added as a chelating agent to the aqueous manicure preparation of the present invention. Further, a defoaming agent other than polydimethylsiloxane described above, an inorganic pigment such as titanium oxide, iron oxide, an organic pigment, a surfactant, a water-soluble organic solvent and the like can suitably be added in a range in which troubles are not exerted on the dispersion system and in which the effects of the present invention are not damaged.

The aqueous manicure preparation of the present invention can be prepared by mixing and dispersing the respective components described above in the contents falling in the respective ranges described above by means of a mixing dispersing machine, for example, a bead mill, a homomixer, a disper, an attriter, a ball mill, a sand grinder and the like.

The aqueous manicure preparation of the present invention thus constituted is stored in the liquid storing part of the applicator which is equipped with at least the liquid storing part and the applying member and in which the liquid is transported from the liquid storing part to the applying member by virtue of capillary force.

Figure 1:
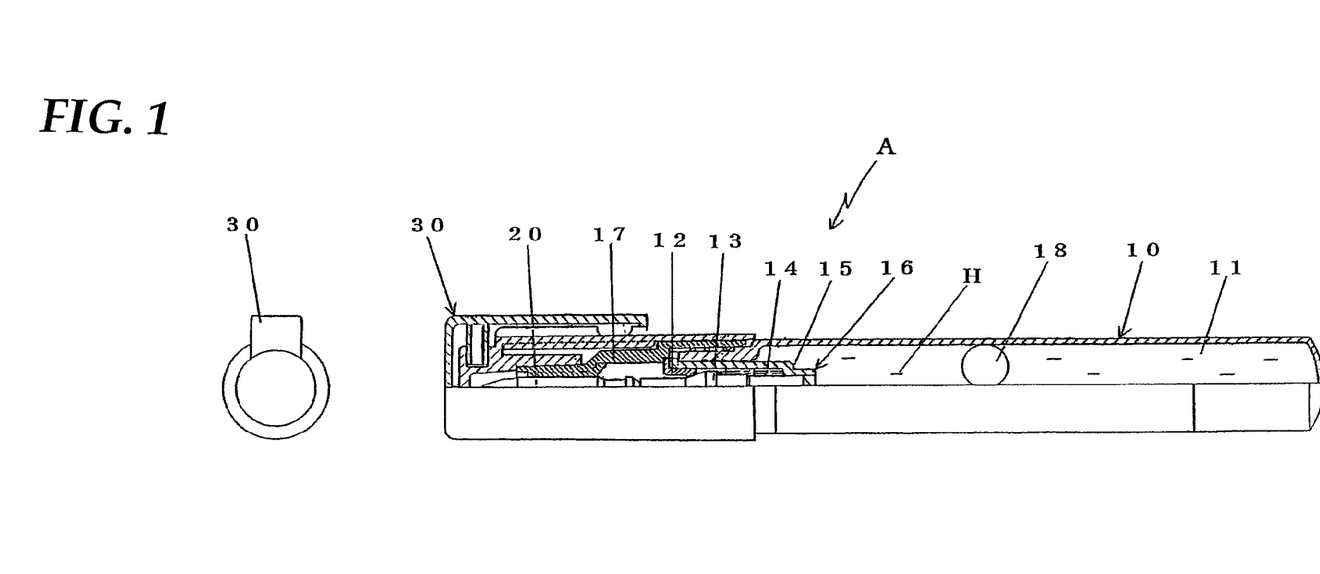
FIG. 1 is a partial vertical cross-sectional drawing and a left face side view which show one example of the embodiment of the aqueous manicure preparation-filled applicator in the present invention.

For example, an applicator A which is equipped, as shown in FIG. 1, with a liquid storing part 11 stored therein with the aqueous manicure preparation constituted above and an applying member 20 having capillary force and in which an aqueous manicure preparation H is transported from the liquid storing part 11 to the applying member 20 by virtue of capillary force can be used as the manicure preparation-filled applicator of the present invention.

To describe the above applicator A in detail, an inside of an applicator main body 10 is the liquid storing part 11; a valve mechanism 16 comprising a valve 12, a valve stem 13, a spring member 14 comprising a coil spring and a spring bearing 15 is provided in a front part of the applicator main body 10, and the applying member 20 described above is slidably held in the inside of a front shaft member 17 mounted in a front part of the applicator main body 10. Meanwhile, a numeral 18 shown in the drawing is a stirring ball made of SUS, and a numeral 30 is a cap body.

Figure 2A:
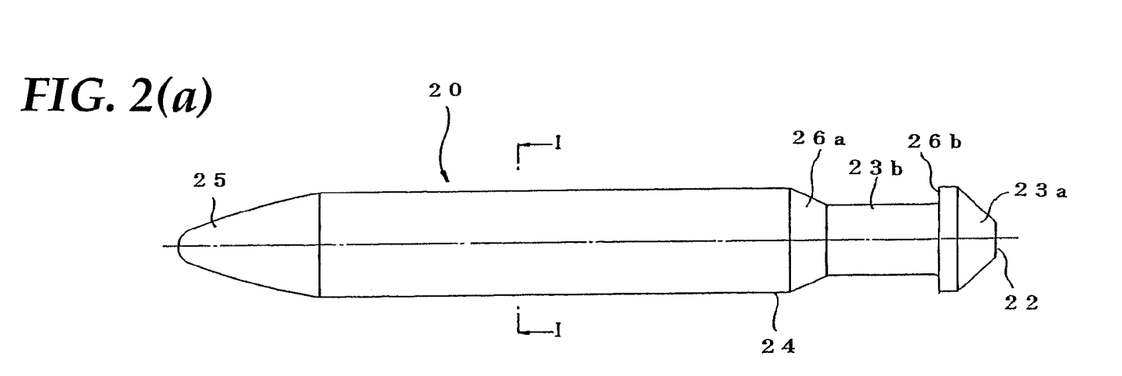
FIG. 2(a) is a side view showing one example of the applicator, and (b) is a I-I line cross-sectional view of (a).
Figure 2B:
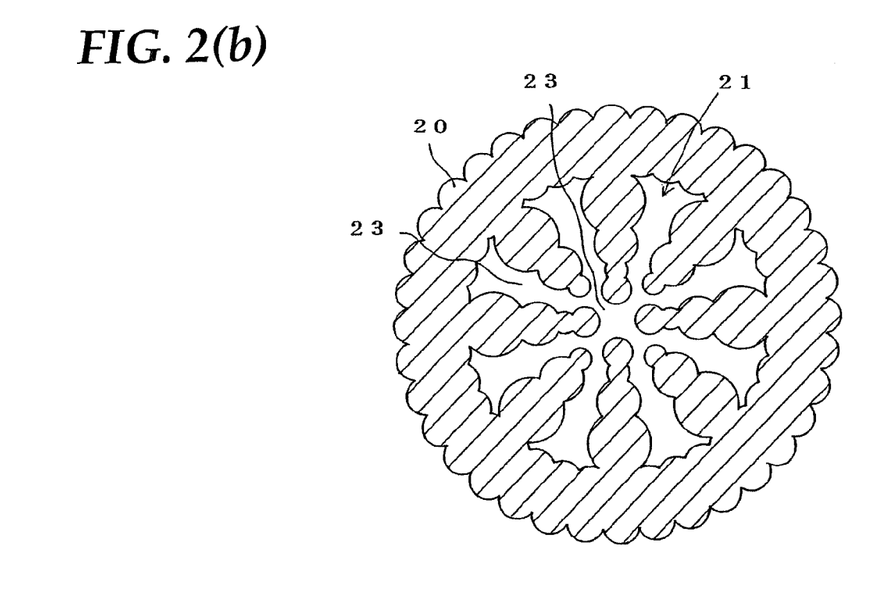

The applying member 20 provided with capillary force is preferably, for example, as shown in FIGS. 2(*a*) and (*b*), a member which is equipped with a tubular inner cylinder 21 and in which an applying tip 25 is conical and is equipped with a slit in a radial pattern. To describe the applying member 20 in detail, a rear end part 22 of the applying member 20 is brought into contact with a front end of the valve stem 13, and the tubular inner cylinder 21 is continuously provided in an axial line direction with a manicure preparation passage 23 of radial inner grooves in a cross section through which the aqueous manicure preparation passes. The above applying member 20 is constituted of a synthetic resin such as polyacetal, and holes 23*a*, 23*b* for introducing the aqueous manicure preparation into the passage 23 in the applying member 20 are formed in the rear end part 22 and a side face part 24 of the applying member. Numerals 26*a*, 26*b* shown in the drawing are a front side face and a rear side face for introducing the aqueous manicure preparation into the passage 23 in the applying member 20.

The valve mechanism 16 is opened by pushing the above applying member 20, and the aqueous manicure preparation H is introduced into the passage 23 in the applying member 20 and supplied to the conical applying tip 25 equipped with a slit in a radial pattern.

In a use mode of the aqueous manicure preparation of the present invention, when the applying member 20 of the applicator A shown in FIG. 1 is pushed, the aqueous manicure preparation H of the present invention is transported from the liquid storing part 11 to the applying member 20, and therefore lines and patterns are drawn directly on a nail or drawn on a coating film of a nail enamel comprising nitrocellulose, a resin, acetic esters and the like applied in advance on a nail. Then, a transparent nail enamel is applied thereon to finish coating, whereby drawing is finished.

At least water, a water-soluble resin, a tabular pigment, an emulsion resin, a moisturizing agent and a fungicide are contained in the aqueous manicure preparation thus constituted according to the present invention, and a surface tension thereof is 33 dyn/cm or less; crystalline cellulose is further contained therein; a viscosity thereof falls in a specific range in a prescribed shear rate at a temperature of 25° C., whereby a tabular pigment is dispersed stably in water, and the preparation is controlled so that prescribed physical properties are provided. Accordingly, provided is the aqueous manicure preparation which is less liable to form a hard cake even when the tabular pigment settles down to make it possible to readily redisperse it by slightly stirring and which is excellent in usability to make it possible to readily draw fine lines and patterns on a nail having a curved surface and excellent in a finishing property.

When fine lines and patterns are drawn on a nail with conventional aqueous manicure preparations, involved therein are the problems that cissing is marked in a case of narrow drawn lines and that in contrast with this, when a relatively broad face is coated, dripping is brought about to make it impossible to draw fine lines and patterns. In the present invention, however, the aqueous manicure preparation is provided with a shear thinning property by controlling a surface tension to 33 dyn/cm or less, further adding the crystalline cellulose and controlling the viscosity to a specific range in a prescribed shear rate at a temperature of 25° C., and therefore capable of being prepared is the aqueous manicure preparation which is reduced in a viscosity when applied on a nail to bring about no cissing even when drawing narrow lines and which is free from dripping to make it possible to readily draw fine lines and patterns and very excellent in an applying performance.

Further, the aqueous manicure preparation-filled applicator of the present invention is equipped with the liquid storing part in which the aqueous manicure preparation having the characteristics described above is stored and the applying member, and the aqueous manicure preparation is transported from the liquid storing part to the applying member by virtue of capillary force. An applying member provided with capillary force is employed as the applying member, whereby provided is the aqueous manicure preparation-filled applicator which is excellent in usability to make it possible to readily draw fine lines and patterns on a nail and which is excellent in a finishing property.

Further, the applying member 20 provided with capillary force is provided with a structure in which it is equipped with the tubular inner cylinder 21 and in which the applying tip 25 is conical and is equipped with a slit in a radial pattern, whereby capable of being prepared is the aqueous manicure preparation-filled applicator which is excellent in usability to make it possible to readily draw finer lines and patterns on a nail and which is very excellent in a finishing property. Meanwhile, the applying member 20 having capillary force is provided with a structure in which it is equipped with the tubular inner cylinder 21 and in which the applying tip 25 is conical and is equipped with a slit in a radial pattern, and in addition thereto, it can be provided as well with a structure having plural opening parts for allowing the aqueous manicure preparation to flow in. Usually, only opening parts (introduction holes 23*a*, 23*b* in the present embodiment) in the other end opposite to the applying tip described above are provided, but a part of a side face of the tubular inner cylinder can be opened by cutting a side face of the applying member to form opening parts. Employing the above constitution makes it possible to secure a passage even in bringing about clogging by the tabular pigment and in addition thereto, makes it possible to allow the aqueous manicure preparation to flow in without a hitch even when troubles such as a rise in a viscosity of the aqueous manicure preparation by vaporization of water and the like are brought about.

Figure 3:
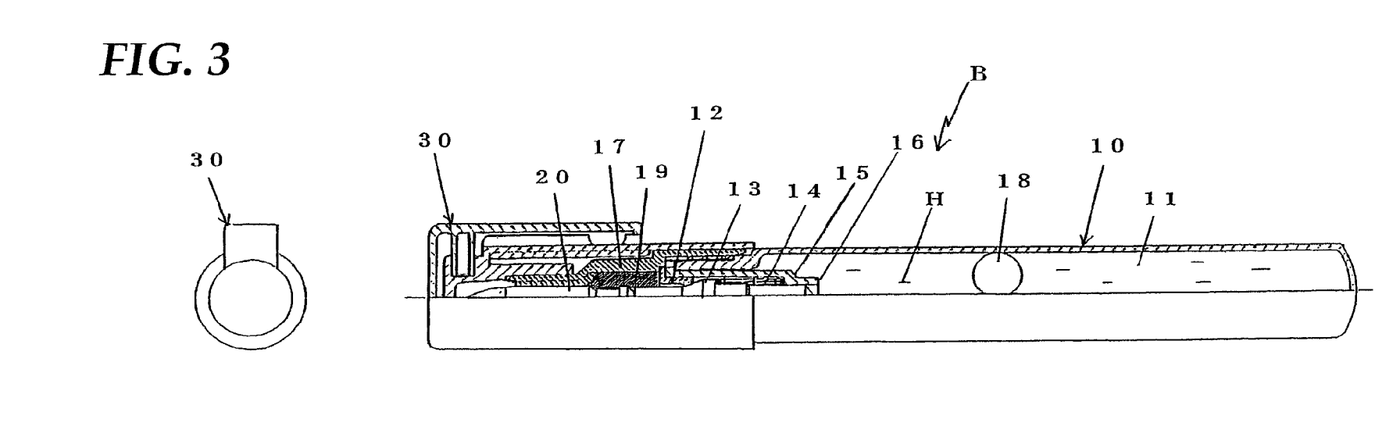
FIG. 3 is a partial vertical cross-sectional view and a left face side view which show another example of the embodiment of the aqueous manicure preparation-filled applicator in the present invention.

Further, the applicator may be, as shown in FIG. 3, an aqueous manicure preparation-filled applicator B in which a porous member having continuous pores (for example, a sponge material) 19 is provided in a passage of the aqueous manicure preparation extending from the liquid storing part 11 to the applying member 20.

In the aqueous manicure preparation-filled applicator B of the present embodiment, the porous member having continuous pores (for example, a sponge material) 19 is provided in a rear of the applying member 20 and a periphery of the valve stem 13. Employing the aqueous manicure preparation-filled applicator B of the above structure makes it possible to supply smoothly and efficiently the aqueous manicure preparation having the characteristics described above to the applying member. For example, when an excess amount of the aqueous manicure preparation flows out due to opening of the valve mechanism 16 in FIG. 1 more than necessary, it becomes possible to hold temporarily the excess amount thereof by the porous member 19 having continuous pores, and dripping of the aqueous manicure preparation from the applying member 20 can be prevented.

EXAMPLES

Next, the present invention shall be explained in further details with reference to examples and comparative examples, but the present invention shall not be restricted to the examples shown below.

Examples 1 to 13 and Comparative Examples 1 to 7

Blending components shown in the following Table 1 and Table 2 were mixed and dispersed by means of a homomixer or a disper to prepare the respective aqueous manicure preparations (blending unit: % by mass, total amount: 100% by mass).

The respective aqueous manicure preparations obtained were used to measure a viscosity in a prescribed shear rate, an n value (non-Newtonian viscosity index) and a surface tension and evaluate usability, precipitation stability, redispersibility and a finishing property.

Measuring Method of Viscosity:

The respective aqueous manicure preparations obtained were used to measure a viscosity in a prescribed shear rate at a temperature of 25° C. by means of a cone plate type viscometer (among TV-30 viscometers, an ELD type viscometer or an EMD type viscometer, each equipped with a standard cone plate, manufactured by Tokimec Inc.) (measured by means of an EHD type viscometer only in Comparative Example 5).

Calculating Method of n Value (Non-Newtonian Viscosity Index):

First, a shear stress S at each shear rate was determined from the following equation (II) applied to a Newtonian liquid:

$$S = \mu D \quad (II)$$

(references in the equation (II) mean the same as in the equation (I)).

Power regression calculation was carried out by using the corresponding list of the shear stress S and the shear rate D which were obtained from the equation (I) in the respective examples and comparative examples to calculate the n value (non-Newtonian viscosity index).

Measuring Method of Surface Tension:

The respective aqueous manicure preparations obtained were used to measure a surface tension at a temperature of 25° C. by means of a full automatic surface tension meter (CBVP-Z, manufactured by Kyowa Interface Science Co., Ltd.).

Evaluation Method of Usability:

The respective aqueous manicure preparations obtained were filled in an applicator shown in FIG. 3, and lines were drawn on a nail to evaluate drawing feeling and a drawn line density according to the following criteria.

Evaluation Criteria:
○: liable to be drawn and has a satisfactory density
Δ: a little faded and blurred but judged to be within a practical range
x: faded and blurred and felt to be unsatisfactory Evaluation Method of Precipitation Stability:

A test tube equipped with a stopper was charged with the respective aqueous manicure preparations and tightly sealed. It was left standing still at 25° C. for one month to observe the presence of separation of the liquid with the naked eye, and a proportion (%) of a color material layer volume to a liquid volume was determined by (height of the color material layer/height of the filled liquid)×100 and evaluated according to the following criteria.

Evaluation Criteria:
○: 40% or more
Δ: 20% or more and less than 40%
x: less than 20%

Evaluation Method of Redispersibility:

The applicator shown in FIG. 3 was charged with the respective aqueous manicure preparations and left standing still at 50° C. for one month. This was shaken with a hand to observe movement of the stirring ball, and it was evaluated according to the following criteria.

Evaluation Criteria:
○: the stirring ball was moved by shaking once to three times
Δ: the stirring ball was moved by shaking four to nine times
x: it was after shaking the applicator 10 times or more that the stirring ball was moved Evaluation Method of Finishing Property:

The applicator shown in FIG. 3 was charged with the respective aqueous manicure preparations, and lines were drawn on a nail to evaluate a finishing property according to the following criteria.

Evaluation Criteria:
○: lines which were fine and free of cissing were drawn
Δ: lines were a little inferior but drawn in an intended manner
x: drawn lines were disordered and not smooth, and cissing was marked

TABLE 1

| Kind | Name | Example 1 | 2 | 3 | 4 | 5 | 6 | 7 |
|---|---|---|---|---|---|---|---|---|
| Thickener | Crystalline cellulose*[1] | 2 | 1.5 | 2.5 | 2 | 2 | 2 | 2 |
| | Xanthan gum | | | | | | | |
| Fungicide | Phenoxyethanol | 0.6 | 0.6 | 0.6 | 0.6 | 0.6 | 0.6 | 0.6 |
| | Methyl paraben | 0.2 | 0.2 | 0.2 | 0.2 | 0.2 | 0.2 | 0.2 |
| | Ethyl paraben | 0.1 | 0.1 | 0.1 | 0.1 | 0.1 | 0.1 | 0.1 |
| Moisturizing agent | 1,3-Pentylene glycol | 5 | 5 | 5 | 5 | 5 | 5 | 5 |
| | 1,3-Butylene glycol | 5 | 5 | 5 | 5 | 5 | 5 | 5 |
| Chelating Agent | Disodium ethylenediamine-tetraacetate | 0.19 | 0.19 | 0.19 | 0.19 | 0.19 | 0.19 | 0.19 |
| Surface tension controlling agent | Sodium dioctyl sulfosuccinate | 0.5 | 0.5 | 0.5 | 0.5 | 0.5 | 0.5 | 0.5 |

TABLE 1-continued

| Kind | Name | | | | | | | |
|---|---|---|---|---|---|---|---|---|
| Emulsion resin | Alkyl acrylate copolymer emulsion*2 | 20 | 20 | 20 | 20 | 25 | 20 | 20 |
| Water-soluble resin | Alkyl acrylate copolymer*3 | 0.5 | 0.4 | 1 | 0.5 | 0.5 | 0.5 | 0.5 |
| Neutralizing agent | 2-Amino-2-methyl-1-propanol | 0.12 | 0.1 | 0.24 | 0.12 | 0.12 | 0.12 | 0.12 |
| Tabular pigment | Iron oxide red-titanium dioxide coated mica | 12 | | | 5 | | 0.5 | 30 |
| | Iron oxide red-black iron oxide-titanium dioxide coated mica | | 5 | | | 12 | | |
| | Iron oxide red-coated silica | | | 15 | | | | |
| | Titanium dioxide-coated mica | | | | 7 | | | |
| Defoaming agent | Polydimethylsiloxane*4 | 0.0007 | 0.0007 | 0.0007 | 0.0007 | 0.0007 | 0.0007 | 0.0007 |
| | Purified water | balance | balance | balance | balance | balance | balance | balance |
| Physical property value | Viscosity shear rate (/s) | | | | | | | |
| 1 | 3.83 | 66.1 | 59.1 | 70.3 | 62.5 | 74.1 | 46.8 | 141 |
| 5 | 19.15 | 26.1 | 25.3 | 34.2 | 27.6 | 40.8 | 20 | 46.2 |
| 10 | 38.3 | 20.82 | 19.4 | 27.4 | 21.44 | 33.62 | 14.89 | 30.22 |
| 20 | 76.6 | 16.3 | 15.9 | 22.4 | 17.09 | 24.15 | 11.65 | 24.4 |
| 100 | 383 | 11.1 | 10.2 | 12.7 | 11.8 | 13.3 | 8.4 | 19.4 |
| n value (non-Newtonian viscosity index) | | 0.62 | 0.62 | 0.63 | 0.64 | 0.63 | 0.63 | 0.57 |
| Surface tension (dyn/cm) | | 30 | 30 | 30 | 30 | 30 | 30 | 30 |
| Usability | | ○ | ○ | ○ | ○ | ○ | ○ | Δ |
| Precipitation stability | | ○ | ○ | ○ | ○ | ○ | ○ | ○ |
| Redispersibility | | ○ | ○ | ○ | ○ | ○ | ○ | ○ |
| Finishing | | ○ | ○ | ○ | ○ | ○ | Δ | Δ |

| | | Example | | | | | |
|---|---|---|---|---|---|---|---|
| Kind | Name | 8 | 9 | 10 | 11 | 12 | 13 |
| Thickener | Crystalline cellulose*1 | 2 | 2 | 2 | 2 | 2 | 2 |
| | Xanthan gum | | | | | | |
| Fungicide | Phenoxyethanol | 0.6 | 0.6 | 0.6 | 0.6 | 0.6 | 0.6 |
| | Methyl paraben | 0.2 | 0.2 | 0.2 | 0.2 | 0.2 | 0.2 |
| | Ethyl paraben | 0.1 | 0.1 | 0.1 | 0.1 | 0.1 | 0.1 |
| Moisturizing agent | 1,3-Pentylene glycol | 5 | 5 | 5 | 3 | 10 | 5 |
| | 1,3-Butylene glycol | 5 | 5 | 5 | 3 | 10 | 5 |
| Chelating Agent | Disodium ethylenediamine-tetraacetate | 0.19 | 0.19 | 0.19 | 0.19 | 0.19 | 0.19 |
| Surface tension controlling agent | Sodium octyl sulfosuccinate | 0.5 | 0.5 | 2.5 | 0.5 | 0.5 | 0.5 |
| Emulsion resin | Alkyl acrylate copolymer emulsion*2 | 5 | 40 | 20 | 20 | 20 | 20 |
| Water-soluble resin | Alkyl acrylate copolymer*3 | 0.5 | 0.5 | 0.5 | 0.5 | 0.5 | 0.5 |
| Neutralizing Agent | 2-Amino-2-methyl-1-propanol | 0.12 | 0.12 | 0.12 | 0.12 | 0.12 | 0.12 |
| Tabular pigment | Iron oxide red-titanium dioxide coated mica | 12 | 12 | 12 | 12 | 12 | 12 |
| | Iron oxide red-black iron oxide-titanium dioxide coated mica | | | | | | |
| | Iron oxide red-coated silica | | | | | | |
| | Titanium dioxide-coated mica | | | | | | |
| Defoaming agent | Polydimethylsiloxane*4 | 0.0007 | 0.0007 | 0.0007 | 0.0007 | 0.0007 | — |
| | Purified water | balance | balance | balance | balance | balance | balance |
| Physical property value | Viscosity shear rate (/s) | | | | | | |
| 1 | 3.83 | 82.7 | 90 | 70.7 | 52.8 | 71.7 | 67.1 |
| 5 | 19.15 | 27.9 | 46 | 33.4 | 21 | 34.6 | 26.8 |
| 10 | 38.3 | 19.95 | 36 | 27 | 16.3 | 30.1 | 20.37 |
| 20 | 76.6 | 14.39 | 30.6 | 20.55 | 12.7 | 22.6 | 17.2 |
| 100 | 383 | 9.3 | 14.8 | 12.8 | 9.33 | 13 | 12.6 |
| n value (non-Newtonian viscosity index) | | 0.53 | 0.62 | 0.63 | 0.62 | 0.63 | 0.64 |
| Surface tension (dyn/cm) | | 30 | 30 | 24 | 30 | 30 | 30 |
| Usability | | ○ | Δ | ○ | Δ | Δ | Δ |
| Precipitation stability | | ○ | ○ | ○ | ○ | ○ | ○ |
| Redispersibility | | ○ | ○ | ○ | ○ | ○ | ○ |
| Finishing | | Δ | ○ | Δ | Δ | Δ | ○ |

TABLE 2

| Kind | Name | Comparative Example | | | | | | |
|---|---|---|---|---|---|---|---|---|
| | | 1 | 2 | 3 | 4 | 5 | 6 | 7 |
| Thickener | Crystalline cellulose*[1] | 2 | 2 | 2 | 2 | 0.2 | 8 | |
| | Xanthan gum | | | | | | | 0.2 |
| Fungicide | Phenoxyethanol | 0.6 | 0.6 | 0.6 | 0.6 | 0.6 | 0.6 | 0.6 |
| | Methyl paraben | 0.2 | 0.2 | 0.2 | 0.2 | 0.2 | 0.2 | 0.2 |
| | Ethyl paraben | 0.1 | 0.1 | 0.1 | 0.1 | 0.1 | 0.1 | 0.1 |
| Moisturizing agent | 1,2-Pentylene glycol | 5 | 5 | 5 | — | 5 | 5 | 5 |
| | 1,3-Butylene glycol | 5 | 5 | 5 | — | 5 | 5 | 5 |
| Chelating Agent | Disodium ethylenediamine-tetraacetate | 0.19 | 0.19 | 0.19 | 0.19 | 0.19 | 0.19 | 0.19 |
| Surface tension controlling agent | Sodium octyl sulfosuccinate | 0.5 | 0.5 | 0 | 0.5 | 0.5 | 0.5 | 0.5 |
| Emulsion resin | Alkyl acrylate copolymer emulsion*[2] | 20 | 20 | 20 | 20 | 20 | 20 | 20 |
| Water-soluble resin | Alkyl acrylate copolymer*[3] | | 5 | 0.5 | 0.5 | 0.5 | 0.5 | 0.5 |
| Neutralizing Agent | 2-Amino-2-methyl-1-propanol | | 1.2 | 0.12 | 0.12 | 0.12 | 0.12 | 0.12 |
| Tabular pigment | Iron oxide red-titanium dioxide coated mica | | | | | | | |
| | Iron oxide red-black iron oxide-titanium dioxide coated mica | | | | | | | |
| | Iron oxide red-coated silica | | | | | | | |
| | Titanium dioxide mica | | | | | | | |
| Defoaming agent | Polydimethylsiloxane*[4] | 0.0007 | 0.0007 | 0.0007 | 0.0007 | 0.0007 | 0.0007 | 0.0007 |
| | Purified water | balance | balance | balance | balance | balance | balance | balance |
| Physical property value | Viscosity shear rate (/s) | | | | | | | |
| 1 | 3.83 | 85.4 | 139 | 65.3 | 50.3 | Immeasurable | 14580 | 131.8 |
| 5 | 19.15 | 31.7 | 80.6 | 25.8 | 19.8 | " | 6200 | 88.6 |
| 10 | 38.3 | 23.35 | 56.42 | 20.6 | 15.4 | " | 4220 | 64 |
| 20 | 76.6 | 16.67 | 43.4 | 15.9 | 11.3 | " | Immeasurable | 42.7 |
| 100 | 383 | 10.5 | 27 | 10.8 | 9 | " | " | 17.3 |
| n value (non-Newtonian viscosity index) | | 0.54 | 0.64 | 0.55 | 0.62 | — | 0.46 | 0.55 |
| Surface tension (dyn/cm) | | 30 | 30 | 35 | 30 | 30 | 30 | 30 |
| Usability | | ○ | ○ | ○ | x | ○ | x | ○ |
| Precipitation stability | | x | ○ | ○ | ○ | x | ○ | x |
| Redispersibility | | x | ○ | ○ | ○ | x | ○ | x |
| Finishing | | x | x | x | x | ○ | x | x |

*[1] to *[4] in Tables 1 and 2 described above show the following:
*[1] Ceolus RC-N81, manufactured by Asahi Kasei Chemicals Corporation
*[2] Yodosol GH800F, solid content: 45% by mass, manufactured by Nihon NSC Co., Ltd.
*[3] Luvimer 100P, manufactured by BASF AG.
*[4] KS-66, manufactured by Shin-Etsu Silicones Co., Ltd.

As apparent from the results shown in Tables 1 and 2 described above, it has been found that the aqueous manicure preparations prepared in Examples 1 to 13 according to the present invention are excellent in usability, precipitation stability, redispersibility and a finishing property as compared with those prepared in Comparative Examples 1 to 7 falling outside the present invention.

To observe individually the comparative examples, Comparative Example 1 is a case in which the water-soluble resin is not added; Comparative Examples 2 and 5 to 6 and Comparative Example 7 in which the xanthan gum is used as a thickener are cases in which a range of the viscosity in a prescribed shear rate in measuring a viscosity at a temperature of 25° C. by means of an ELD type viscometer or an EMD type viscometer is deviated from the range of the present invention; Comparative Example 3 is a case in which the surface tension is deviated from the range of the present invention; and Comparative Example 4 is a case in which the moisturizing agent is not added. It has been found that the effects of the present invention can not be achieved in the above examples.

INDUSTRIAL APPLICABILITY

The aqueous manicure preparation of the present invention makes it possible to readily draw fine lines and patterns on a nail and is excellent in a finishing property and usability, and therefore it can suitably be used for an aqueous manicure preparation and an applicator filled with the above manicure preparation.

LIST OF REFERENCE NUMERALS

A Aqueous manicure preparation-filled applicator
H Aqueous manicure preparation
10 Applicator main body
11 Liquid storing part
16 Valve mechanism
17 Front shaft member
18 Stirring ball
20 Applying member
25 Applying tip (applying part)
30 Cap member

What is claimed is:

1. An aqueous manicure preparation comprising water; a water-soluble resin comprising a copolymer of tert-butyl acrylate, ethyl acrylate and methacrylic acid; a tabular pigment selected from the group consisting of mica or a tabular pigment coated with metal or metal oxide selected from the group consisting of: mica, titanium dioxide coated mica, carmine-titanium dioxide coated mica, carmine-Prussian blue-titanium dioxide coated mica, black iron oxide-titanium dioxide coated mica, black iron oxide-carmine-titanium dioxide coated mica, black iron oxide-Prussian blue-titanium dioxide coated mica, Prussian blue-titanium dioxide coated mica, iron oxide red-coated mica, iron oxide red-titanium dioxide coated mica, iron oxide red-carmine-titanium dioxide coated mica, iron oxide red-black iron oxide-titanium dioxide coated mica, iron oxide red-Prussian blue-titanium dioxide coated mica, iron oxide red-black iron oxide-Prussian blue-titanium dioxide coated mica, a brilliant pigment prepared by coating metal or metal oxide on a glass flake or a massive flake used as a base material and iron oxide red coated silica; an emulsion resin; a moisturizing agent; and
a fungicide; wherein the aqueous manicure preparation has a surface tension of 33 dyn/cm or less; wherein the tabular pigment is a powder and is present in a content of 1 to 20% by mass based on a total amount of the aqueous manicure preparation; wherein the aqueous manicure preparation further comprises crystalline cellulose; and wherein the aqueous manicure preparation satisfies the following condition (A) in measuring the viscosity at a temperature of 25° C. by means of a cone plate type viscometer:

| (A) shear rate ($s^{-1}$) | viscosity (mPa · s) |
|---|---|
| 3.83 | 30 to 150 |
| 19.15 | 10 to 50 |
| 38.30 | 10 to 40 |
| 76.60 | 10 to 40 |
| 383.00 | 5 to 20. |

2. The aqueous manicure preparation as described in claim 1, wherein a value of n in the following equation (I) falls in a range of 0.5 to 0.7:

$$S = \mu D^n \quad (I)$$

in the equation (I), S is a shear stress (Pa); $\mu$ is a viscosity coefficient (viscosity: Pa·s); D is a shear rate ($s^{-1}$); and n is a non-Newtonian viscosity index.

3. The aqueous manicure preparation as described in claim 1, wherein the water-soluble resin accounts for 0.008 to 2.0% by mass; the emulsion resin accounts for 4.5 to 13.5% by mass in terms of a solid content; and a total of the fungicides accounts for 0.01 to 10.0% by mass.

4. The aqueous manicure preparation as described in claim 1, wherein the crystalline cellulose accounts for 0.5 to 10.0% by mass.

5. The aqueous manicure preparation as described in claim 1, wherein the moisturizing agent accounts for 8 to 15% by mass.

6. The aqueous manicure preparation as described in claim 1, wherein the aqueous manicure preparation further contains at least polydimethylsiloxane.

7. An aqueous manicure preparation-filled applicator which is equipped with a liquid storing part stored with the aqueous manicure preparation as described in claim 1 and an applying member and in which the aqueous manicure preparation is transported from the liquid storing part to the applying member by virtue of capillary force, wherein the applying member is provided with capillary force.

8. The aqueous manicure preparation-filled applicator as described in claim 7, wherein the applying member provided with capillary force is equipped with a tubular inner cylinder, and a tip thereof is conical and is provided with a slit in a radial pattern.

9. The aqueous manicure preparation-filled applicator as described in claim 7, wherein a porous member having continuous pores is provided in a passage of the aqueous manicure preparation extending from the liquid storing part to the applying member.

10. An aqueous manicure preparation-filled applicator which is equipped with a liquid storing part stored with the aqueous manicure preparation as described in claim 1, a stirring ball, a valve mechanism, and an applying member which is equipped with a slit in a radial pattern, wherein the aqueous manicure preparation is transported from the liquid storing part to the applying member by opening the valve mechanism by pushing the applying member backward, and wherein the aqueous manicure preparation is transported to an applying tip from the applying member by capillary force.

* * * * *